United States Patent

Rossignol

[11] Patent Number: 6,020,353
[45] Date of Patent: Feb. 1, 2000

[54] 2-(HYDROXY)-N-(5-NITRO-2-THIAZOLYL) BENZAMIDE

[75] Inventor: Jean-Francois Rossignol, Clearwater, Fla.

[73] Assignee: Romark Laboratories, L.C., Tampa, Fla.

[21] Appl. No.: 09/170,697

[22] Filed: Oct. 13, 1998

Related U.S. Application Data

[62] Division of application No. 08/847,130, May 1, 1997, Pat. No. 5,886,013, which is a continuation of application No. 08/383,855, Feb. 16, 1995, abandoned, which is a continuation-in-part of application No. 08/301,407, Sep. 8, 1994, Pat. No. 5,578,621.

[51] Int. Cl.$^7$ ...................................................... A01N 43/78
[52] U.S. Cl. ............................................ 514/371; 514/370
[58] Field of Search ....................................... 514/370, 371

[56] References Cited

U.S. PATENT DOCUMENTS 3,950,351  4/1976  Rossigaol et al. .................... 200/306.8

OTHER PUBLICATIONS

Murphy, James R., 1–Pharmacology, vol. 102, 1985, 102:197602b, Pre clinical toxicology of nitazoxanide—a new antiparasitic compound.

Cavier, Raymond, et al., Recherches sue les dérivés nitrés d'intérêt biologique, Eur. J. Med. Chem. —Chimca Therapeutica, Nov.–Dec., 1978–13, No. 6, pp. 539–543.

Miller, Wayne, H., Chemical Abstracts vol. 115, 1991, 115:201471j, Guanosine Kinase from *Trichomonas vaginalis*.

Dymicky, M., et al., Inhibition of Clostridium botulinum by 5–Nitrothiazoles, Antimicrobial Agents and Chemotherapy, Sep. 1977, pp. 353–356.

Husain, et al., Chemical Abstracts, vol. 93, 1980, 93:114374a Search for potent anthelmintics, Part XIII.

Husain et al. 93 CA114374a, 1979.

Cavion et al Eur J. Med Chem, vol. 13167 pp. 539–543, 1978.

Dymicky et al, Anti Micro & Chems, vol. 12(3) pp. 353–356, 1977.

*Primary Examiner*—Russell Travers
*Attorney, Agent, or Firm*—Pendorf & Cutliff

[57] ABSTRACT

The present invention relates to a pharmaceutical composition containing a compound of formula I

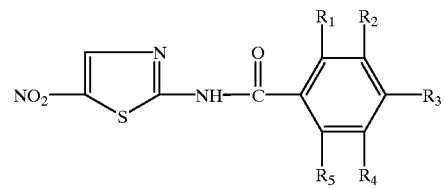

with one of the symbols $R_1$, $R_2$, $R_3$, $R_4$ and $R_5$ representing OH, whereas the remaining symbols represent H as antiviral agent.

3 Claims, 2 Drawing Sheets

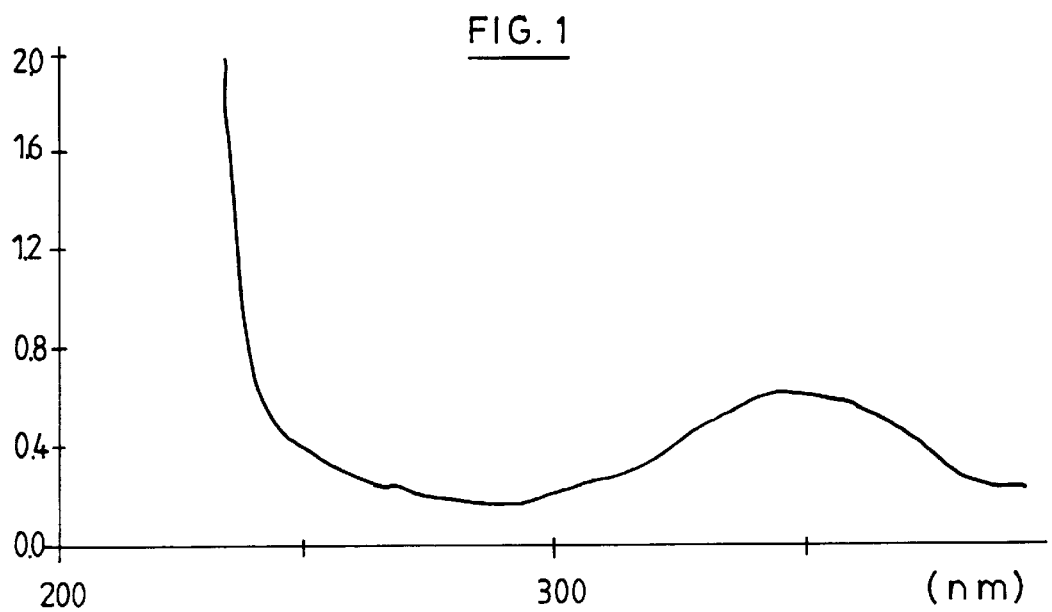
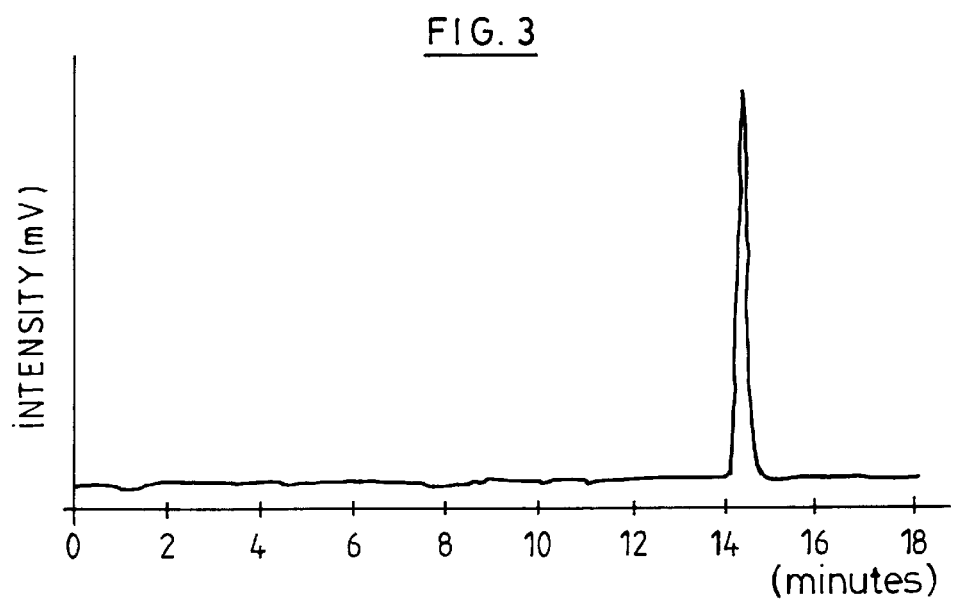

2-(HYDROXY)-N-(5-NITRO-2-THIAZOLYL) BENZAMIDE

This is a divisional of application Ser. No. 08/847,130 filed May 1, 1997, now U.S. Pat. No. 5,886,013 allowed Jul. 21, 1998, which is a continuation of Ser. No. 08/383,855 now abandoned filed Feb. 6, 1995, which is a continuation in part of 08/301,407 filed Sep. 8, 1994, now U.S. Pat. No. 5,578,621.

THE PRIOR ART

Nitrothiazole compound PH 5776 (2-(acetolyloxy)-N-(5-nitro 2-thiazolyl) benzamide) is a compound of formula II

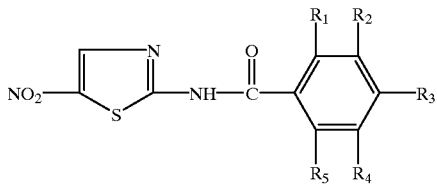

in which $R_1$=O—COCH$_3$ $R_2=R_3=R_4=R_5=H$

The preparation and uses of this compound are disclosed in U.S. Pat. No. 3,950,351, as well as in publication made by Applicant.

In U.S. Pat. No. 3,950,351, the compound of formula II is prepared by reacting

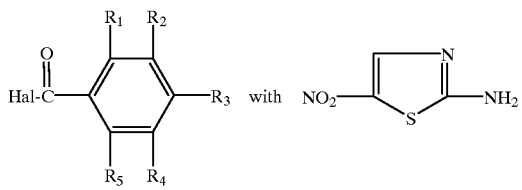

This reaction is not suitable for the preparation of pure compound of formula I

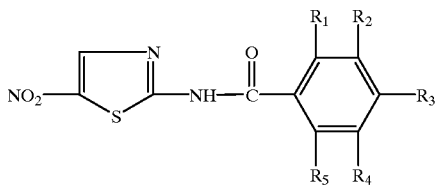

in which one of the symbols $R_1$, $R_2$, $R_3$, $R_4$ and $R_5$ represents OH, whereas the remaining symbols represent H.

In application U.S. Pat. No. 08/301407 filed on Sep. 8, 1994 in the name of Applicant, the scope of which is incorporated herewith by reference, it has been disclosed that the compound of formula I

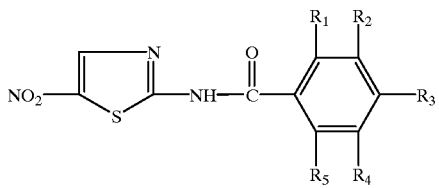

with one of the symbols $R_1$, $R_2$, $R_3$, $R_4$ and $R_5$ representing OH, whereas the remaining symbols represent H; has an excellent efficiency against parasites, bacteria, fungus, although it does not contain an acyloxy group, said compound of formula I having a substantially immediate action against parasite, fungus, bacteria.

BRIEF DESCRIPTION OF THE INVENTION

The present invention relates to a pharmaceutical composition suitable for treating viral diseases, for example human viral infections, or for preventing such trouble, the composition containing as active agent a compound of the following formula

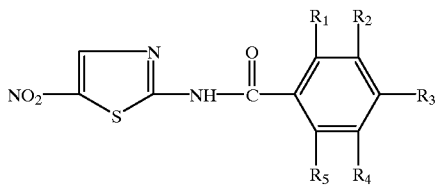

in which one of the symbols $R_1$, $R_2$, $R_3$, $R_4$ and $R_5$ represents OH, whereas the remaining symbols represent H. Preferably, $R_1$=OH.

According to an embodiment, the composition comprises, as active agent, a mixture comprising a compound A of formula

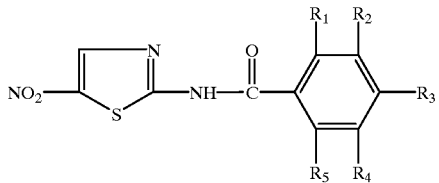

with $R_1$=OH and $R_2=R_3=R_4=R_5=H$ and a compound B of formula

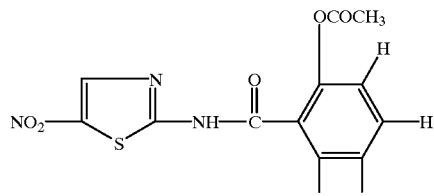

Such a composition combines a substantially immediate action against viruses or a substantially immediate treatment of liver trouble and a somewhat retarded action or treatment.

Such a composition is thus suitable for treating human viral infections, such as diseases of the liver.

In said composition, the weight content of compound A of formula

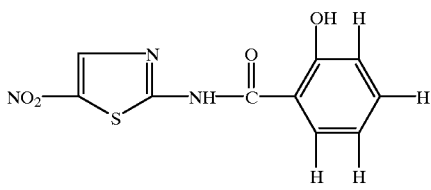

with respect to the weight of a mixture of compound A of formula

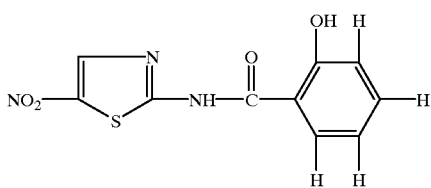

and compound B of formula

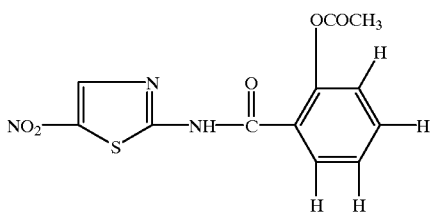

is comprised between 1 and 20%, preferably between 1 and 10%, more preferably between 1 and 5%.

The invention relates also to the use of a compound A, especially in the form of a composition according to the invention, as antiviral agent.

DESCRIPTION OF THE DRAWINGS

FIG. 1 is the UV of compound A of formula

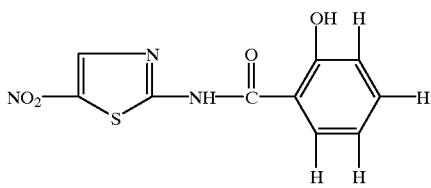

Figure 2:
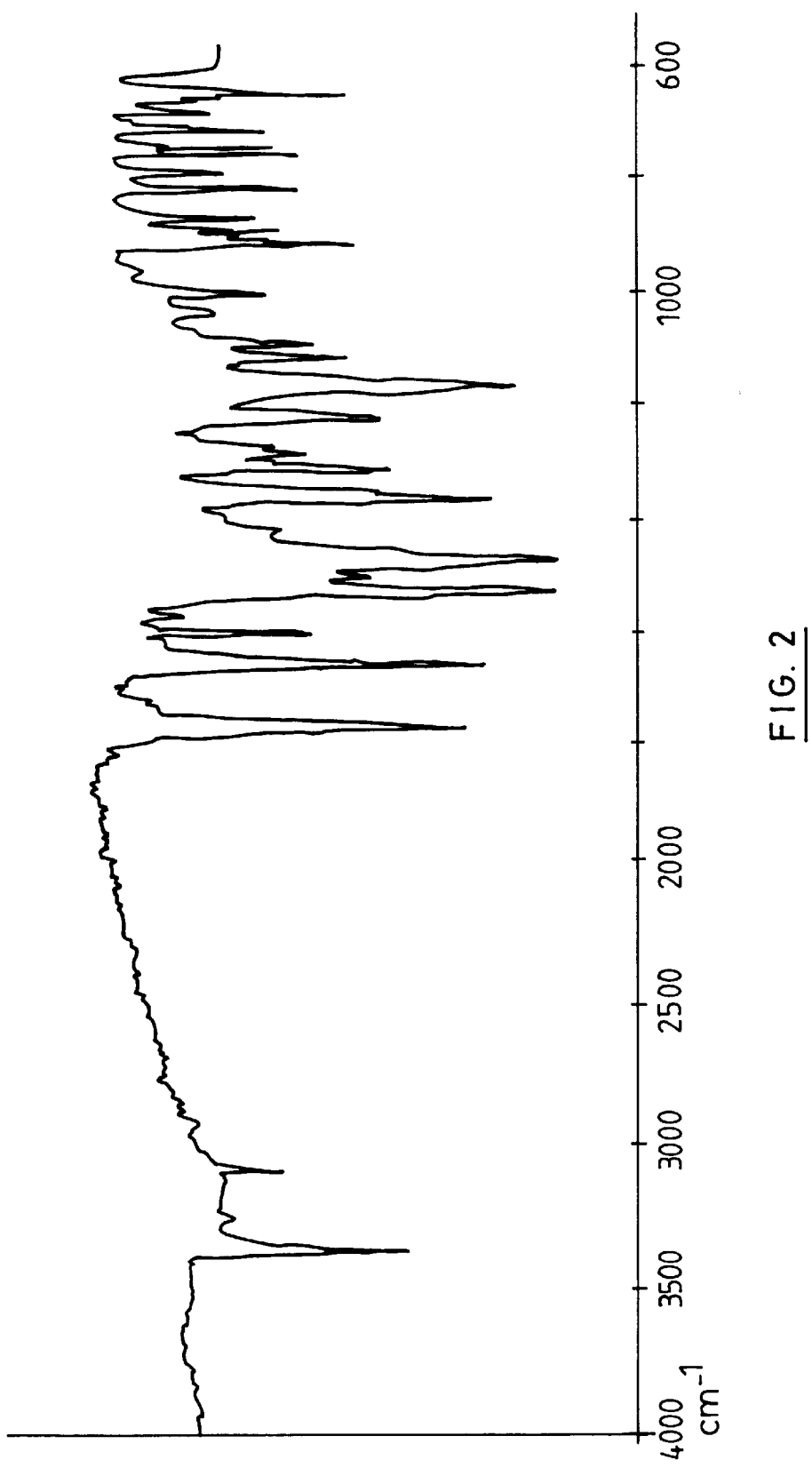

FIG. 2 is the IR spectrum of the said compound A, and

FIG. 3 is the GC- mass spectrum of the said compound A.

DESCRIPTION OF THE INVENTION

The preparation of pure compound of formula

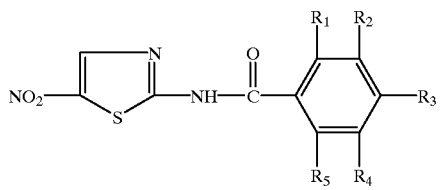

in which one of the symbols $R_1$, $R_2$, $R_3$, $R_4$ and $R_5$ represents OH, whereas the remaining symbols represent H, can be made from compounds of formula II

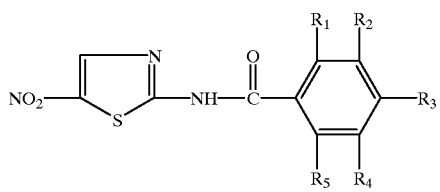

in which one of the symbols $R_1$, $R_2$, $R_3$, $R_4$ and $R_5$ is an acyloxy group, whereas the remaining symbols represent hydrogen.

The said compound of formula II is put in suspension in a weak mixture of hydrochloridric acid and water. The so treated compound is then filtered and washed with water. The washed compound is then possibly dried.

A specific example of preparation is given hereafter:

2 g of 2-(acetolyloxy)-N-(S-nitro 2-thiazolyl) benzamide (i.e. PH 5776) prepared according to the method disclosed in U.S. Pat. No. 3,950,351 is put in suspension in 20 ml of a 37% HCl solution. The medium was kept at 50° C. during 24° C. and was slowly stirred.

After said treatment, the medium was filtered so as to obtain solid particles. Said particles have then been washed with water until pH 7 and dried in an oven at 50° C.

The resulting product appears as yellow microcristalline needles, the melting point of which was 254° C. (melting point measured according to the capillary determination on a Mettler FP apparatus).

The structure identification was carried out by centesimal analysis, UV spectrum (see FIG. 1), IR spectrum (see FIG. 2) and gas-chromatography-mass spectrum (see FIG. 3). The results of this identification are:

C10, H7, N3, O4, S1; 258 Calculated C 46,51% H 2,71% N 16,40% S 12,40% found 45,98% 2,63% 16,71% 12,67% $\lambda_{max}$=350 nm (OD=0.605).

A composition according to the invention has been prepared by mixing PH 5776 and the compound prepared hereabove, the weight content of said compound with respect to the weight of the said compound and PH 5776 being 4% for this specific example.

Compound A of formula has been tested so as to determine its in vitro antiviral properties.

General procedures for determining Antiviral Efficiency and Toxixity are given hereafter.

Laboratory Procedures for Determining Antiviral Efficacy and Toxicity

A. Preparation of Human Foreskin Fibroblast Cells

Newborn human foreskins were obtained as soon as possible after circumcisions were performed and placed in minimal essential medium (MEM) containing vancomycin, fungizone, penicillin, and gentamycin, at the usual concentrations, for four hours. The medium was then removed, the foreskins minced into small pieces and washed repeatedly until red cells were no longer present. The tissue was then trypsinized using trypsin at 0.25% with continuous stirring for 15 minutes at 37° C. in a $CO_2$ incubator. At the end of each 15 minutes period the tissue was allowed to settle to the bottom of the flask. The supernatant containing cells was poured through sterile cheesecloth into a flask containing MEM and 10% fetal bovine serum. The flask containing the medium was kept on ice throughout the trypsinizing procedure. After each addition of cells, the cheese cloth was washed with a small amount of MEM containing serum. Fresh trypsin was added each time to the foreskin pieces and the procedure repeated until no more cells became available. The cell containing medium was then centrifuged at 1000 RPM at 4° C. for ten minutes. The supernatant liquid was discarded and the cells resuspended in a small amount of MEM with 10% FBS (Fetal Bovine Serum). The cells were then placed in an appropriate number of 25 cm² tissue culture flasks. As cells became confluent and needed trypsinization, they were gradually expanded into larger flasks. The cells were kept on vancomycin and fungizone to passage four.

B. Cytopathic Effect Inhibition Assay—HSV, HCMV, VZV

Low passage human foreskin fibroblast cells were seeded into 96 well tissue culture plates 24 hours prior to use at a cell concentration of $2.5 \times 10^4$ cells per ml in 0.1 ml of minimal essential medium (MEM) supplemented with 10% fetal bovine serum (FBS). The cells were then incubated for 24 h at 37° C. in a $CO_2$ incubator. After incubation, the medium was removed and 100 µl of MEM containing 2% FBS was added to all but the first row. In the first row, 125 µl of experimental drug was added in triplicate wells. Medium alone was added to both cell and virus control wells. The drug in the first row of wells was then diluted serially 1:5 throughout the remaining wells by transferring 25 µl using the Cetus Liquid Handling Machine. After dilution of drug, 100 µl of the appropriate virus concentration was added to each well, excluding cell control wells which received 100 µl of MEM. For HSV-1 and HSV-2 assays, the virus concentration utilized can be 1000 PFU's per well. For CMZ and VZV assays, the virus concentration added can be 2500 PFU's per well. The plates were then incubated at 37° C. in a $CO_2$ incubator for three days for HSV-1 and HSV-2, or 10 days for VZV, or 14 days for CMV. After the incubation period, media was aspirated and the cells stained with a 0.1% crystal violet solution for 30 minutes. The stain was then s removed and the plates rinsed using tap water until all excess stain was removed. The plates were allowed to dry for 24 h and then read on a Skatron Plate Reader at 620 nm.

C. Plaoue Reduction Assay for HSV-1 and HSV-2 Using Semi-Solid Overlay

Two days prior to use, HFF (Human Foreskin Fibro blast) cells are plated into six well plates and incubated at 37° C. with 5% $CO_2$ and 90% humidity. On the date of assay, the drug is made up at twice the desired concentration in 2× MEM and then serially diluted 1:5 in 2× MEM and then serially diluted 1:5 in 2× MEM using six concentrations of drug. The initial starting concentration is usually 200 µg/ml down to 0.06 µg/ml. The virus to be used is diluted in MEM containing 10% FES to a desired concentration which will give 20–30 plaques per well. The media is then aspirated from the wells and 0.2 ml of virus is added to each well in duplicate with 0.2 ml of media being added to drug toxicity wells. The plates are then incubated for one hour with shaking every fifteen minutes. After the incubation period, an equal amount of 1% agarose was added to a equal volume of each drug dilution. This will give final drug concentrations beginning with 100 µg/ml and ending with 0.03 µg/ml and a final agarose overlay concentration of 0.5%. The drug agarose mixture is applied to each well in 2 ml volume and the plates then incubated for three days, after which the cells were stained with a 1.5% solution of neutral red. At the end of 4–6 hr incubation period, the stain is aspirated, and plaques counted using a stereomicroscope at lox magnification.

$EC_{50}$ (50% effective concentration) is the concentration required to inhibit viral cytopathogenicity by 50%. $IC_{50}$ (50% inhibitory concentration) is the concentration required to inhibit cell proliferation by 50%. Selective Index (S.I.)= $IC_{50}/EC_{50}$.

D. VZV Plaque Reduction Assay—Semi-Solid Overlay

The procedure is essentially the same as for the HSV plaque assay described above with two exceptions:
1. After addition of the drug, the plates are incubated for ten days.
2. On days three and six an additional 1 ml overlay with equal amounts of 2× MEM and 1% agarose are added.

E. CMV Plaque Assay—Semi-Solid Overlay

The procedure again is nearly the same as for HSV with a few minor changes. The agarose used for both the initial overlay and the two subsequent overlays is 0.8% rather than 1%. The assay is incubated for 14 days with the additional 1 ml overlays being applied on days four and eight.

F. Plaque Reduction Assays Using Liquid Medium Overlay

The procedure for the liquid overlay plaque assay is similar to that using the agarose overlay. The procedure for adding the virus is the same as for the regular plaque assay. The drugs area concentration to be used in MEM with 2% FBS. The drugs are not made up at 2× concentration as in the previous assays but are made up at the desired concentration. For HSV-1 and HSV-2 assays, an antibody preparation obtained from Baxter Health Care Corporation is diluted 1:500 and added to the media that the drug is diluted in. For CMV and VZV, no antibody in the overlay is utilized. For the CMV assay, additional medium without new drug is added on day five and allowed to incubate for a total of 10 days. For VZV, additional media is added on day five and incubated for a total of 10 days. At the end of the incubation period for all of the assays, 2 ml of a 1:10 dilution of stock neutral is added to each well and incubated for six hours. The liquid is then aspirated off and plaques enumerated using a stereomicroscope.

G. Screening and Confirmation Assays for EBV

1. Virus

There are two prototypes of infectious EBV.

One is exemplified by the virus derived from supernatant fluids of the P3HR-1 cell line. This cell line produces nontransforming virus that causes the production of early antigen (EA) after primary infection or superinfection of B cell lines. The other prototype is exemplified by the B-95-8 virus. This virus immortalized cord blood lymphocytes and induced tumors in marmosets. It does not, however, induce an abortive productive infection even in cell lines harboring EBV genome copies. The virus used in our assays is P3HR-1.

2. Cell Lines

Ramos is an exceptional B cell line derived from Burkitt's lymphoma tumor but containing no detectable EBV genome copies and is EBNA negative. Ramos/AW was obtained by in vitro infection of Ramos with the P3HR-1 virus and contains one resident EBV genome copy/cell. Raji is a Burkitt's lymphoma cell line containing 60 EBV genomes/ cell, and will be the primary cell used for screening antiviral activity against EBV EA expression. Daudi is a low level producer that contains 152 EBV genome copies/cell. It spontaneously expresses EBV EA in 0.25%–0.5% of the cells. It will be used in follow-up studies to confirm activity. These cell lines respond to superinfection by EBV by expressing EA(D), EA(R), and VCA. All cell lines are maintained in RPMI-1640 medium supplemented by 10% FCS, L-glutamine and 100 $\mu$g/ml gentamicin. The cultures are fed twice weekly and the cell concentration adjusted to $3\times10^5$/ml. The cells are kept at 37° C. in an humidified atmosphere with 3. Immunofluorescence Assays with Monoclonal Antibodies Cells are infected with the P3HR-1 strain of EBV and the drugs to be tested are added after adsorption (45 minutes at 37° C.) and washing of the cell cultures. The cultures are incubated for two days in complete medium to allow viral gene expression. Following the 48 hours incubation period, the number of cells of each sample are counted and smears made. Monoclonal antibodies to the different EA components and VCA are then added to the cells incubated and washed. This is followed by a fluorescein conjugated rabbit anti-mousse Ig antibody; and, the number of fluorescence positive cells in the smears are counted. The total number of cells in the cultures positive for EA or VCA are then calculated and compared.

H. Cell Proliferation Assay—Toxicity

Twenty four hours prior to assay, HFF cells are seeded in 6-well plates at a concentration of $2.5\times10^4$ cells per well in MEM containing 10% FBS. On the day of the assay, drugs are diluted serially in MEM containing 10% FES at increments of 1:5 covering a range from 100 $\mu$g/ml to 0.03 $\mu$g/ml. For drugs that have to be solubilized in DMSO, control well receive MEM containing 10% DMSO. The media from the wells is then aspirated and 2 ml of each drug concentration is then added to each well. The cells are then incubated in a $CO_2$ incubator at 37° C. for 72 hours. At the end of this time, the media-drug solution is removed and the cells washed. One ml of 0.25% trypsin is added to each well and incubated until the cells start to come off of the plate. The cell-media mixture is then pipetted up and down vigorously to break up the cell suspension and 0.2 ml of the mixture is added to 9.8 ml of Isoton III and counted using a Coulter Counter. Each sample is counted three times with three replicate wells per sample.

I. MTT Assay for Cell Cytotoxicity

Twenty-four hours prior to Assay, HFF cells are plated into 96 well plates at a concentration of $2.5\times10^4$, cells per well. After 24 hours, the media is aspirated and 125 microliters of drug is added to the first row of wells and then diluted serially 1:5 using the automated Cetus Liquid Handling System in a manner similar to that used in the CPE assay. The plates are then incubated in a $CO_2$ incubator at 37° C. for seven days. At this time, each well receives 50 microliters of 1 $\mu$g/ml solution of MTT in Dulbecco's Phosphate Buffered Saline. The plates are then incubated for an additional four hours. At this time, the media is removed and replaced with 100 $\mu$l of 0.04N hydrochloric acid in isopropanol. After shaking briefly, the plates are then read on a plate reader at 550 nm.

J. Neutral Red Uptake Assay—Toxicity

The procedure for plating cells and adding drug is the same as for MTT Assay.

After drug addition, the plates are incubated for seven days in a $CO_2$ incubator at 37° C. At this time the media/drug is aspirated and 200 $\mu$l/well of 0.01% neutral red in DPBS is added. This is incubated in the $CO_2$ incubator for one hour. The dye is aspirated and the cells are washed using a Nunc Plate Washer. After removing the DPBS wash, 200 $\mu$g/well of 50% ETOH (ethanol)/1% glacial acetic acid (in $H_2O$) is added. The plates are rotated for 15 minutes and the optical densities are read at 550 nm on a plate reader.

Test I

Antiviral Activity Against HBV Replication in Cultures (Hepatites B)

The protocol for Assaying anti-HBV compounds in cultures of 2.2.15 cells can be briefly summarized as follows (Korba and Milman, 1991, Antiviral Res. 217:217):

Chronically HBV-producing human liver cells (Acs, et al, 1987, PNAS 84:4641) are seeded into 24 well tissue culture plates and grown to confluence.

Test compounds are then added daily for a continuous 9 day period. Culture medium (changed daily during the treatment period) is collected and stored for analysis of extracellular (virion) HBV DNA after 0,3,6 and 9 days of treatment.

Treated cells are lysed 24 hours following day 9 of treatment for the analysis of intracellular HBV genomic forms.

HBV DNA is then analyzed in a quantitative and Qualitative manner for overall levels of HBV DNA (both extracellular and intracellular DNA) and the relative rate of HBV replication (intracellular DNA).

The protocol for determining toxicity of compounds in cultures of 2.2.15 cells can be briefly summarized as follows (Korba and Gerin, submitted for publication):

2.2.15 cells were grown to confluence in 96 well fat-bottomed tissue culture plates and treated with compounds (in 0.2 ml culture medium/well) as described above. Four concentrations of each compound were assayed, each in triplicate cultures, 3 to 10-fold steps.

Untreated control cultures were maintained on each 96 well plate. On each 96 well plate, wells containing no cells were used to correct for light scattering.

Toxicity was determined by the inhibition of the uptake of neutral red dye, determined by absorbance at 510 nanometers relative to the absorbance for untreated cells (Finter et al., 1969, *J. Med. Chem.* 5:419), 24 hours following day 9 of treatment.

The antiviral activity of compound A has been compared with that of zalcitabine.

It was found that when using compound A, the effective concentration (EC 50) was 1.8±0.1 microgram/ml ($\mu$g/l) for having a 50% inhibit of viral cytopathogenicity, while the cytotoxic concentration (for having a 50% inhibit of cell proliferation) was greater than 1000 $\mu$g/ml. The selective index SI for compound A was thus equal to >1000/1.8, i.e. a index higher than 500.

For Zalcitabine, the tests showed the following results:

EC 50:1.8±0.2 $\mu$g/ml

CC 50:261±24 $\mu$g/ml i.e. a selective index SI of 261/1.8 i.e. about 145.

As it can be seen from this text, Compound A was less toxic than Zalcitabine, whereby a more appropriate treatment with less secondary effects can be obtained against HBV replication.

Test II
Antiviral Activity Against VZV

A mixture of Nitazoxanide (96%) and compound A (4%) was also used in order to determine its activity against a Varicella Zoster Virus (a standard laboratory strain).

It was found a EC50 of 4 μg/ml and a CC50 of 34 μg/ml, for the said mixture against said Varicella Zoster Virus, i.e. a S.I. index of about 8.5.

In view of the low toxicity and the efficiency of the mixture, the mixture was particularly suitable for the treatment of Varicella Zoster Virus known as resistant to antiviral agent such as Acyclovir.

Composition according to the invention which comprises advantageously compound PH 5776, may also contain a further antiviral agent, such as zalcitabine, acyclovir, ganciclovir, etc so as to have the broad spectrum as possible of activity.

Compound A and the composition according to the invention can be administrated orally, for example by means of tablets.

The compositions of the invention, espescially those containing PH 5776 and/or a further antiviral agent are compositions having a broad spectrum of action on Herpes viruses such as:

- HERPES SIMPLEX VIRUS TYPE 1 (HSV-1, HSV-1 resistant to acyclovir);
- HERPES SIPLEX VIRUS TYPE 2 (HSV-2, HSV-2 resistant acyclovir);
- HUMAN CYTOMEGALOVIRUS (HCMV, HCMV resistant to ganciclovir);
- VARICELLA ZOSTER VIRUS (VZV, VZV resistant to acyclovir);
- EPSTEIN BARR VIRUS (EBV);
- MURINE CYTOMEGALOVIRUS (MCMV).

The compositions can contain excipients known as such for the purpose of preparing forms suitable for oral administration.

The compositions contain advantageously a wetting agent and possibly a starch derivative such as those disclosed in U.S. Pat. No. 08/227033, the content of which is incorporated herein by reference for disclosing possible wetting agents and starch derivatives.

What I claim is:

1. Compound (A):

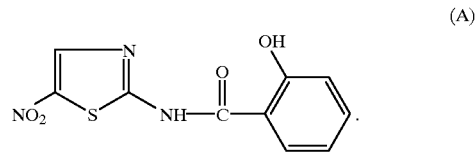

(A)

2. A pharmaceutical composition comprising, as active agent, compound (A):

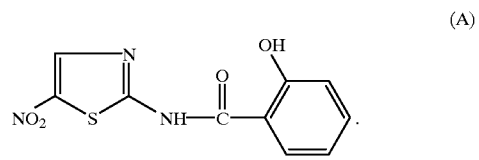

(A)

3. A pharmaceutical composition consisting essentially of, as active agent, compound (A):

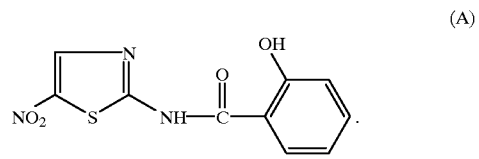

(A)

* * * * *